United States Patent [19]

Smith

[11] Patent Number: 5,735,266
[45] Date of Patent: *Apr. 7, 1998

[54] INSULATED CONDITIONED RESPIRATORY AIR TRANSPORT TUBE

[76] Inventor: Charles A. Smith, 811 Starlite Dr., Louisville, Ky. 40207

[*] Notice: The term of this patent shall not extend beyond the expiration date of Pat. No. 5,377,670.

[21] Appl. No.: 578,439

[22] Filed: Dec. 26, 1995

Related U.S. Application Data

[63] Continuation-in-part of Ser. No. 367,733, Jan. 3, 1995, which is a continuation-in-part of Ser. No. 900,995, Jun. 19, 1992, Pat. No. 5,377,670, which is a continuation-in-part of Ser. No. 593,555, Oct. 9, 1990, abandoned, which is a continuation-in-part of Ser. No. 275,940, Nov. 25, 1988, abandoned, which is a continuation-in-part of Ser. No. 19,248, Feb. 26, 1987, abandoned, which is a continuation-in-part of Ser. No. 910,625, Sep. 23, 1986, abandoned.

[51] Int. Cl.$^6$ .............. A61M 16/00; A62B 7/00; A62B 9/06; F24J 3/00

[52] U.S. Cl. .............. 128/204.18; 128/207.14; 128/204.17

[58] Field of Search .............. 128/204.17, 204.18, 128/201.13, 207.14, 911, 912; 604/163, 171, 263; 138/122

[56] References Cited

U.S. PATENT DOCUMENTS

| 3,383,875 | 5/1968 | Haas | 128/204.17 |
| 4,013,122 | 3/1977 | Long | 128/204.17 |
| 4,415,389 | 11/1983 | Medford et al. | 138/121 |
| 5,377,670 | 1/1995 | Smith | 128/204.17 |

*Primary Examiner*—Kimberly L. Asher

[57] ABSTRACT

The present invention includes a method for preventing heat loss or gain from a conditioned air transport tube in a patient temperature control system thereby reducing internal and/or external vapor condensation commonly associated with such patient temperature control systems while also stabilizing the relative temperature and humidity within such temperature control systems. A thin flexible partially longitudinally compressed casing is provided to surround a corrugated tube of the same or greater thickness to provide an insulating dead air space therebetween. In another arrangement selected enlarged corrugations are provided in spaced relation along the corrugated tube to engage the inner surface of the casing in a preselected spaced arrangement with respect to said corrugated tube to compartmentalize insulating dead air spaces between the tube and the casing.

3 Claims, 5 Drawing Sheets

INSULATED CONDITIONED RESPIRATORY AIR TRANSPORT TUBE

CROSS REFERENCE TO RELATED APPLICATIONS

This application is a continuation-in-part of my Application U.S. Ser. No. 08/367,733 filed Jan. 3, 1995 which is continuation-in-part of U.S. Ser. No. 07/900,995 filed Jun. 19, 1992 (now U.S. Pat. No. 5,377,670), which is a continuation-in-part of U.S. Ser. No. 593,555 filed Oct. 9, 1990 (abandoned) which is a continuation-in-part of U.S. Ser. No. 275,940 filed Nov. 25, 1988 (abandoned) which is a continuation-in-part of U.S. Ser. No. 019,248, filed Feb. 26, 1987 (abandoned) which in turn is a continuation in part of my U.S. Ser. No. 910,625 filed Sep. 23, 1986 (abandoned). Each of the above patents and applications is incorporated herein by reference as if its full printed text appeared hereinafter.

BACKGROUND OF THE INVENTION

The present invention relates to a patient temperature conditioning system having a conditioned air transport tube comprising a corrugated tube and a casing for reduction of heat transfer to or from the corrugated tube. Such tubes are commonly utilized with patient temperature control systems which include a source of conditioned air (either heated or cooled) and an air distribution blanket or tube on top of or in close proximity to a patient. Briefly, the invention includes a tubular sleeve or casing which encloses an air impervious conduit inside the casing in such a manner that a dead air space is created between the outside of the conduit and the inside of the casing. The linear volume of the dead air space is in a ratio to the linear volume of the conduit it encompasses of in the range of 0.5 to 1.0 to approximately 10.0 to 1.0 with 1–2 to 1.0 being common.

Various type tubular and conduit arrangements are presently in use for the delivery of conditioned air to a patient temperature control system. Such systems are commonly used for the control of a patient's body temperature before, during and immediately after surgery and in various other care areas of a hospital. A complete patient temperature control system usually includes a conditioned air generator, an air filled blanket or U-shaped tube arrangement on or in close proximity to a patient, and a means of transporting conditioned air from the conditioner to the blanket or tube. The conditioned air generator then mechanically controls the flow of gases within the patient system which may also include humidifying and/or temperature adjusting devices interconnected with the system.

A common problem associated with traditional systems is that the distance between the conditioned air source and the patient temperature control device is quite long. The long distance that the conditioned gases must travel through the conduits, from the conditioned air generator to the patient temperature control device frequently allows the gases to fall below, or in the case of cooled air to rise above, the optimal temperature and humidity levels for achieving optimal patient temperature control. Thus, prolonged operation of the system may permit the patient's body temperature to vary from desirable levels.

Attempts have been made to alleviate the aforenoted problem associated with a traditional circuit by placing patient temperature control devices in close proximity to the patient. However, because the area near a post-operation patient is generally already crowded, the presence of such devices in close proximity to a patient in the recovery room causes most attendants and patients to find this arrangement greatly annoying and inconvenient, and potentially dangerous.

In an attempt to alleviate the cumbersomeness of a traditional patient temperature control system, one might turn to tube insulating arrangements used for like purposes in anesthesia circuits. For example, British Patent Publication No. 2,029,703 A, discloses the use of a single limb anesthesia circuit consisting of two corrugated wall tubes, where each tube is affixed at one end to a respirator and at the other to a connector to the patient's airway. Because both inhalation and exhalation tubes were affixed to a connector on the patient side, the inner tube offered resistance and restricted the outer tube when pressure within the inner tube was increased, i.e. as with every forced inhalation by the respirator.

The previously discussed deficiencies of British Patent Publication No. 2,029,703 A were attempted to be rectified in U.S. Pat. No. 4,463,755, to Suzuki. Suzuki defines an inner inhalation tube coaxially circumscribed by an outer exhalation tube, the resistance between the two tubes was minimized by retaining members affixed to the inner tube at a fixed distance. However, there are two major problems associated with a Suzuki-type circuit. First, they are expensive and complex to manufacture, and second, there may be a build-up of liquid condensation and other matter within the exhalation tube which is caused by the difference in the temperature gradient between the patient's exhalant breath and the atmospheric temperature in contact with the exhalant tube.

Further, this condensation provides an environment for germicidal growth when used for prolonged periods. This germicidal growth can be of great concern vis-a-vis the patient, increasing the possibility of complicating infections which increase morbidity and mortality. The aforenoted disadvantageous condensation is commonly associated with almost all traditional breathing circuits.

U.S. Pat. No. 3,814,091 to Henkin teaches a breathing apparatus using a corrugated breathing tube with a flexible tubular enclosure surrounding a portion of the breathing tube but, contrary to the present invention, where there is no air flow between the corrugated hose and the outer casing or sleeve, in Henkin flow conduits or holes are required in the breathing tube to allow air flow into the space between the breathing tube and the envelopes. Consequently, the area between the breathing tube and the tubular enclosure (envelope) of Henkin is not a dead air space, and therefore not insulating as it is in the present invention. In Henkin the outer tube enclosure acts like a balloon which when squeezed by the operator delivers a volume of air to the patient's air stream. Moreover in Henkin, the outer envelope may contain a slit to act as a pressure relief means.

U.S. Pat. No. 2,119,446 like U.S. Pat. No. 3,814,091 relates to a perforated corrugated tube which is surrounded by a balloon.

U.S. Pat. No. 4,269,193 teaches a breathing apparatus with concentric air flow tubes where air flows through the annular area so the area is not a dead air space as provided by the present invention.

U.S. Pat. No. 4,300,547 teaches an inhalation conduit which is covered with a sheath of material which can be wetted with a liquid so the conduit is cooled by evaporation.

Likewise U.S. Pat. No. 3,924,619 teaches a heat exchange means, not an insulating arrangement for breathing conduits.

U.S. Pat. No. 3,185,182 to Waddell relates to a conduit having a corrugated tubular body with a plastic coated circumferential reinforcement containing an additional reinforcement member. The tube does not have a dead air insulating space.

U.S. Pat. No. 3,490,496 to Stearns relates to flexible transfer lines for cryogenic liquids. The coaxial tubing has inner and outer concentrically arranged tubes and spacing means therebetween.

U.S. Pat. No. 2,898,941 to Kilcup provides an inhaler tube having exterior helical corrugations to import maximum flexibility while at the same time maintaining the tube free from kinking with the tube also having a smooth interior surface that readily lends itself to thorough cleansing and sterilization.

U.S. Pat. No. 3,858,615 to Weigl describes a kink-resistant hose construction of a one piece tube of flexible material having a smooth cylindrical inner wall surface for efficient air flow and easy cleaning and having axially spaced concentric rings on its outer wall.

U.S. Pat. No. 4,000,341 to Matson refers to a autoclavable corrugated respiratory air tubing which translucent so that liquid build-up in the tubing can be seen through the walls of the tubing.

U.S. Pat. No. 2,073,335 to Connell is a breathing tube which employs various reinforcements which may be applied by hand or by suitable mechanical means.

U.S. Pat. No. 4,415,389 to Medford suggests an inner corrugated hose construction and a sleeve disposed around the hose having the function of improving the fluid pressure resistance and the external water resistance, the sleeve being taut and free of sags.

U.S. Pat. No. 4,007,737 to Paluch relates to a anesthesia breathing circuit having inner and outer tubes with spacer means for supporting and maintaining the tubes enspaced in relatively fixed spatial relation.

Also various insulating ventilation hoses are suggested by Drs. Alan R. Mizutani, Ozahi, and Rusk in ANESTH ANALG. 1991,72:561–7 but none disclose the insulating features of the present invention.

SUMMARY OF THE INVENTION

Patients in recovery rooms are usually in an air conditioned environment, cooler than their body temperature, both for their own comfort and the comfort of attending personnel. However, the air conditioned atmosphere may cool the patient to a level which is undesirable and detrimental. Moreover, the cool ambient temperature in the recovery room can cause undesirable liquid condensation in the systems.

Consequently, patient temperature control systems have been introduced to hospitals to aid in controlling a patient's body temperature during surgery and thereafter. Such patient temperature control systems are disclosed and described in, for example, U.S. Pat. No. 5,184,612, issued Feb. 9, 1993 and U.S. Pat. No. 4,572,188, issued Feb. 25, 1986 both to Augustine and U.S. Pat. No. 5,304,213, issued Apr. 19, 1994 to Berke. Accordingly, the present invention provides a method of enhancing the operation of a patient temperature control system by stabilizing the thermal gradient and therefore reducing heat losses between the conditioned air and the surrounding atmosphere and reducing condensation commonly associated with such temperature control systems. Consequently, the relative humidity and temperature within such a system are stabilized.

More specifically the invention includes an insulated conditioned air transport tube arrangement having an air impervious corrugated tube for carrying conditioned gases and an outer casing of first internal diameter for insulating the corrugated tube, said corrugated tube being located within said casing and having an outer diameter less than said internal diameter of said casing, said casing being of an overall length greater than the length of said corrugated tube and being sealed at its ends to the ends of the corrugated tube such that the casing is in a slightly longitudinally compressed state relative to said corrugated tube thereby defining an insulating dead air space between said corrugated tube and said casing, said casing further being of a thickness which is equal to or less than the thickness of said corrugated tube.

Within the scope of the present invention are features that are inexpensive, easily fabricated and highly effective to reduce condensation of vapor within a patient temperature control system. Features within the scope of the present invention are particularly useful when utilized with corrugated hoses of the type commonly used to carry conditioned gases to and from a patient warming or cooling apparatus during medical treatment or in the recovery room thereafter. In one embodiment the present invention reduces or eliminates condensation on the outside of the air conducting hose when cold air is being used to cool a patient.

Devices within the scope of the present invention facilitate the maintenance of a prescribed temperature of a patient during an anesthesia/surgical procedure or thereafter.

Moreover, the apparatus of the present invention assists in the maintenance of the normal body temperature of a patient in situations where the normal body temperature is desired since body heat loss may occur by breathing cool gasses present in a closed mechanically assisted breathing circuit.

Devices within the scope of the present invention reduce or totally eliminate problems occurring in patient temperature control systems caused by "rainout", i.e. the condensation and accumulation of liquid inside and outside the conditioned air transport hoses during use.

Devices within the scope of the present invention also maintain the flexibility of the commonly available air hoses and permit visual observation of any condensation which may occur.

Particularly, the present invention provides a method for preventing heat transfer to or from a patient temperature control system to stabilize the thermal gradient between the system and the surrounding atmosphere to reduce internal vapor condensation commonly associated with such systems while also stabilizing the relative humidity within such a system.

In the preferred form a tubular casing or sleeve is provided to surround a corrugated tube of the system to provide insulating dead air space therebetween. In another arrangement selected corrugations are provided in spaced relation along the corrugated tube to engage the inner surface of the casing to define the dead air space.

Also, the casing, being readily removable from the inner hose can be easily removed and replaced if the outer casing becomes soiled. Abraision of the inner hose is also reduced by the outer sleeve which is able to slide on the outer surface of the inner hose. Also, the casing is easily cleanable and can function as simplify clean up either as a easily cleaned item or a disposable item. In this regard, the outer casing may be easily replaced by hand or with a vacuum arrangement which holds the casing open while the corrugated tube is inserted.

While various arrangements within the scope of the present invention are disclosed herein and discussed hereinafter it will be understood that the arrangements are provided for purposes of illustration only and not by way of limitation and that various other arrangements also within the scope of the present invention will occur to those skilled in the art upon reading the disclosure set forth hereinafter.

BRIEF DESCRIPTION OF THE DRAWINGS

Examples within the scope of the present invention are illustrated in the accompanying drawings wherein.

DETAILED DESCRIPTION OF THE DRAWINGS

Figure 1:
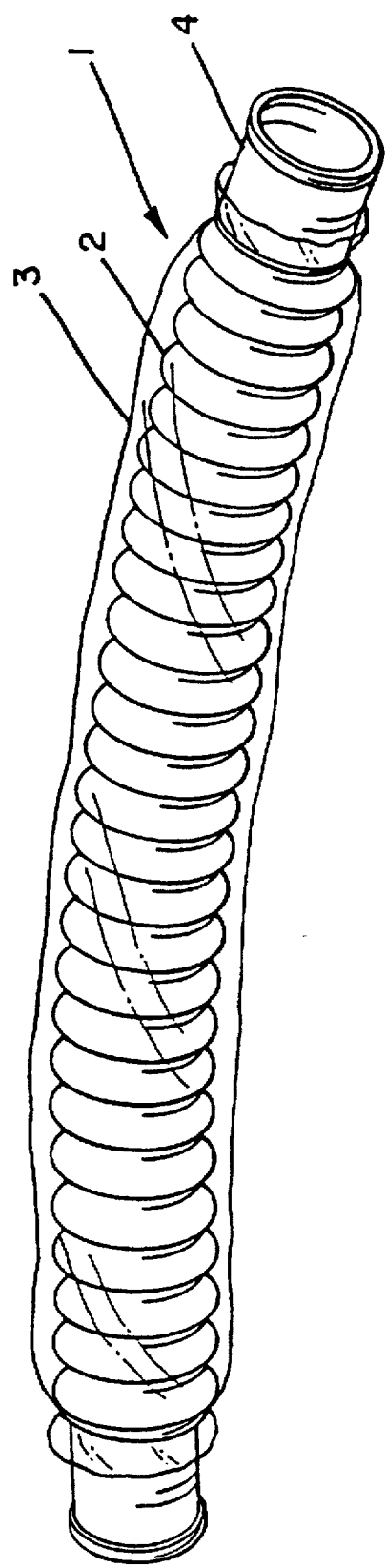
FIG. 1 is a perspective view of a corrugated hose of the type useful within the scope of the present invention showing its encasement by a tubular casing to provide a combination within the scope of the present invention.

Referring first to FIG. 1 a conditioned air transport tube 1 of the type contemplated by the present invention is illustrated where corrugated tube 2 of the type generally known in the art is provided. A casing 3 is provided, as described hereinafter, to encase the tube 2 to define an insulating dead air space between the conditioned air transport tube 2 and the casing 3. A tip 4 is provided at the end of the tube 2 to facilitate connection of the tube either to a source of conditioned air or gas or to a device to deliver the conditioned air to a patient. As is known in the art a similar arrangement can be provided on the other end of the tube and the tube then is utilized to supply conditioned air and gases from the source to the patient. As is also known in the art, the corrugations are provided along the length of the tube to facilitate bending or shaping the tube without risk of stopped gas flow because of kinking.

Figure 2:
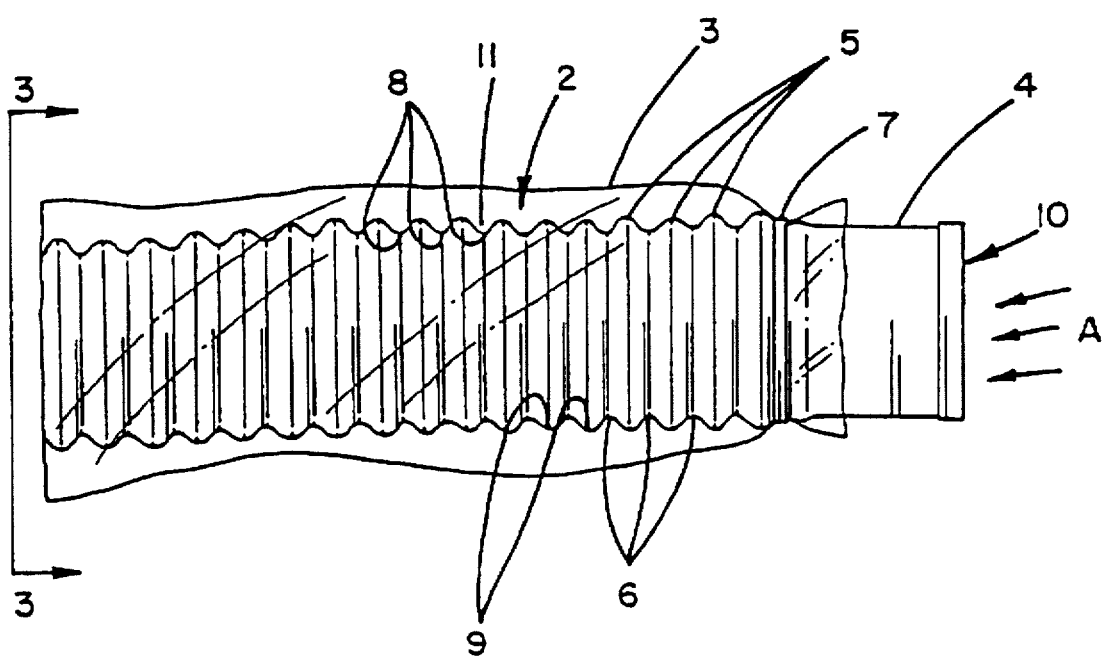
FIG. 2 is an enlarged view of a portion of an arrangement within the scope of the present invention.

FIG. 2 is a view, partially in cross section, of a tube of the type shown in FIG. 1 where the corrugation crests 5 and valleys 6 are shown as is the casing 3.

The casing 3 can be retained on the tube 2 by any convenient means and in the arrangements shown an elastomeric fastener, for example a rubberband 7, or "O" ring is provided to be placed over the outer surface of the casing 3 and received between the raised portions of the tube 2 to hold the casing under the rubberband 7 in one of the valleys between the corrugations.

While other fastening means can be provided the one illustrated in FIG. 2 has been found to be particularly effective and very inexpensive.

There are several features which should be considered in connection with the arrangement shown in FIG. 2, the first of which is that the air represented by the arrows A flows through the opening 10 in the tube and contacts principally the lower indented portions 8 of the corrugations.

As is known in the art the heat transfer occurring in the tube occurs in the area of highest Reynolds number. Since the Reynolds number is dependent on velocity the highest heat transfer will occur in the areas 8 on the inner surface of the corrugations through the indented portions 8 of the corrugations. Conversely, the air trapped in the depressions 9 is generally stagnate compared with the air flowing through opening 10. Since the stagnate air provides some insulation within the tube, less heat transfer occurs through the area 9 in the upstanding portions of the corrugations.

In practice, without the use of the casing 3, heat is transferred through the areas 8 of the corrugated tubing and convective currents flowing through areas 11 facilitate loss of heat through the indented portions 8 to the ambient air surrounding the tube 2.

In accordance with one feature of the present invention it is recognized that by use of the casing 3 these convective currents are prevented so the heat loss which would otherwise occur through the portions 8 of the corrugated tubing is substantially reduced. Further, the casing 3 should have a wall thickness equal to or less than the thickness of the corrugated tubing wall to maintain flexibility of the entire unit yet because of the lack of corrugations the casing substantially reduces the surface area available for convective heat transfer and additionally provides another barrier for radiant heat loss and air currents.

Casing 3 most preferably is clear, as is the corrugated tubing so that the presence of condensate in or on the tube can be monitored visually. Additionally, the overall length of the casing is less than the extended length of the corrugated tubing i.e. when the tubing 2 extended to the point that the sidewalls are no longer corrugated but rather are straight. Thus it can be seen that the surface of the casing is substantially less, by approximately one quarter to one-half, than the surface area of the corrugated tubing to further reduce heat transfer.

Accordingly, the arrangement shown permits the transmission of a stream of air through a relatively long tube with virtually no change in temperature and with very little additional expense, bulk, or loss of flexibility or loss of visual contact with the interior of tube 2.

If any of the previously discussed devices are used to supply heat to the gasses within the tubing to prevent condensation and loss of temperature the features provided by the present invention would enhance the performance of such devices.

It is further recognized that the casing 3 is sized so that it does not contact corrugation crests 5 except on a random basis by gravity.

Figure 3:
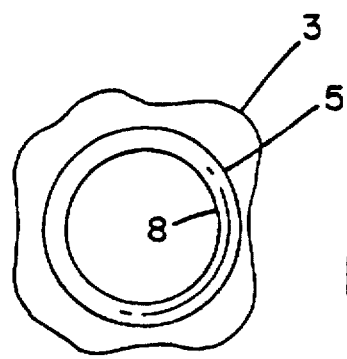
FIG. 3 is a cross sectional view taken along a plane passing through line 3—3 of FIG. 2.

FIG. 3 is a cross sectional view of the conditioned transport tube of FIG. 2 taken along line 3—3 thereof. The loose fitting nature of casing 3 is clearly evident in FIG. 3.

Figure 4:
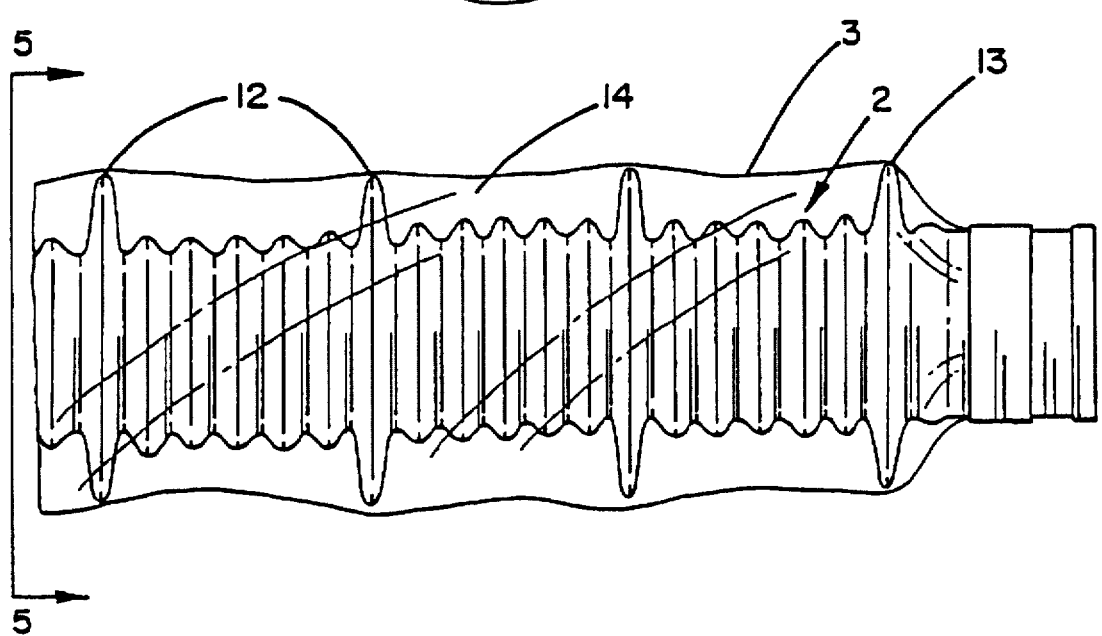
FIG. 4 is an illustration of another arrangement within the scope of the present invention.

FIG. 4 shows another embodiment of the insulated breathing tube assembly of FIG. 1 wherein intermittently spaced corrugations 12 are provided which have outer crests 13 that are substantially greater in height than the corrugations of the tube adjacent thereto. The consequence of providing such intermittently spaced larger corrugations is that it is assures that casing 3 will not contact corrugated tube 2 except at such intermittent corrugations. This arrangement has the effect of maximizing the distance between corrugated tube 2 and casing 3 and compartmentalizing the dead air space between the corrugated tube and the casing. One such compartment is shown at 14 in FIG. 4. It should be noted however, that even in the embodiment of FIG. 4 casing 3 is sized to be loose fitting and not in taut contact with outer crests 13.

Figure 5:
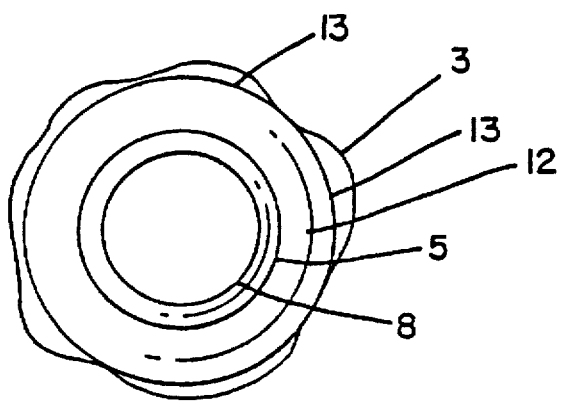
FIG. 5 is a cross sectional view taken along a plane passing through line 5—5 of FIG. 4.

FIG. 5 shows a cross section of the embodiment of FIG. 4 along a plane passing through line 5—5 of FIG. 4 showing intermittently spaced corrugations 12 and outer crests 13.

There are two important features of this invention which will now be more fully described. It is essential in the invention to have the outer casing 3 of a thickness which is equal to or less than the thickness of the inner corrugated tube 2. Further, the outer casing should be of an internal diameter which is greater than the external diameter of the corrugated tube 2. Most preferably the ratio of these diameters is 1 to 2.20 or greater, or expressed in absolute measurements the inner diameter of the casing 3 should be at least two centimeters greater than the external diameter of tube 2 and preferably more depending on the size of the inner corrugated tube.

Figure 6:
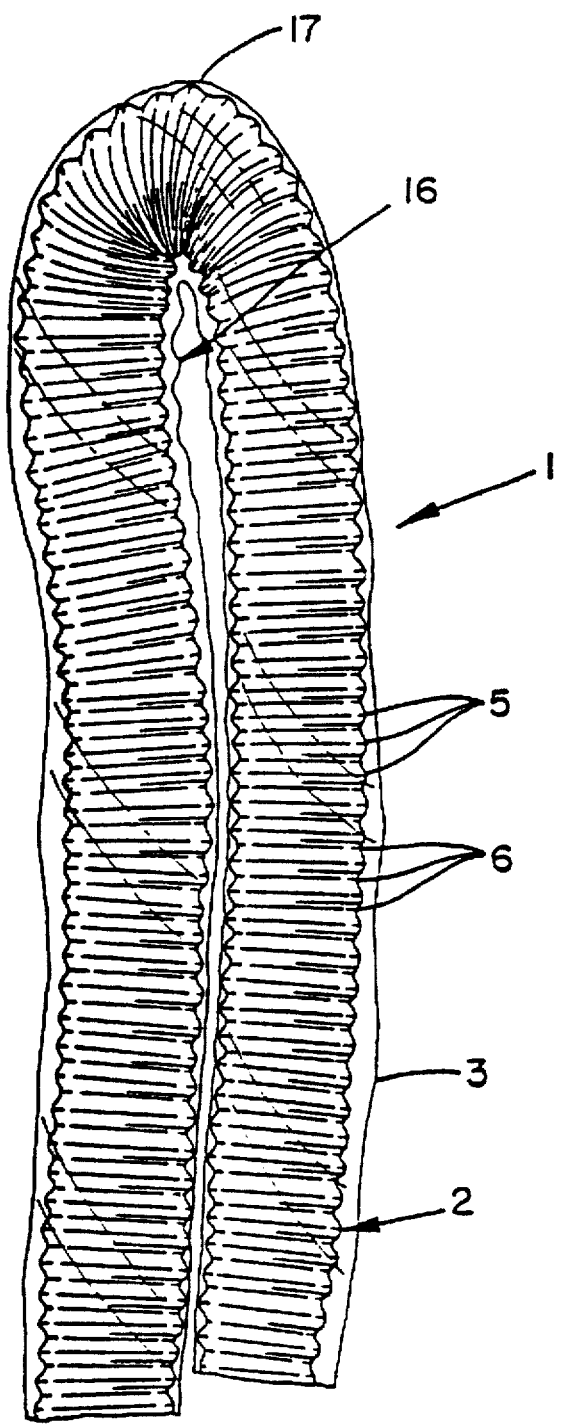
FIG. 6 is an illustration of the insulated conditioned air transport tube of this invention being folded back upon itself in hairpin fashion.
Figure 7:
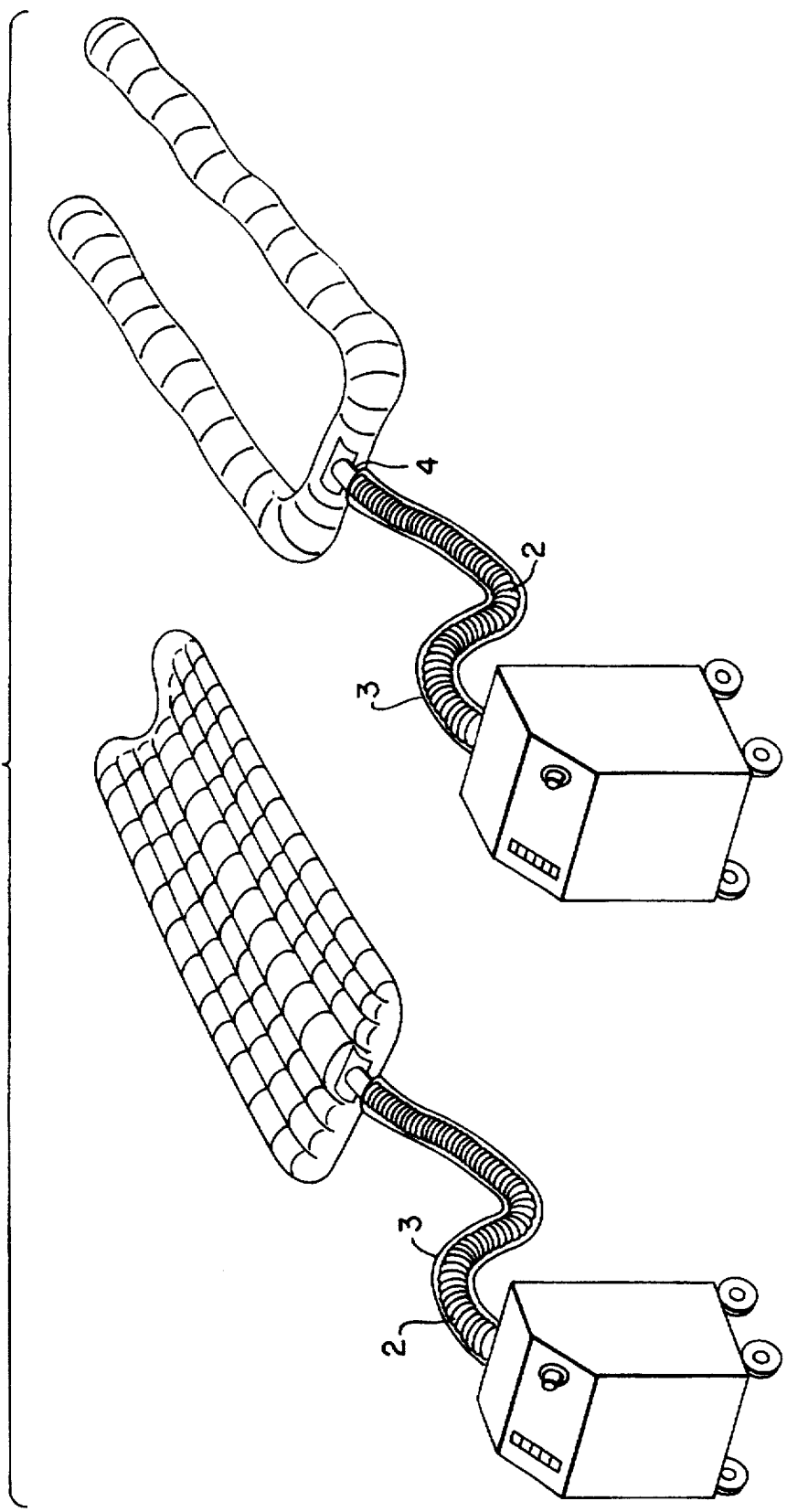
FIG. 7 is a perspective view of the patient temperature control system utilizing the insulated conditioned air transport tubes of this invention.

The reason for the greater diameter and thinner material is that frequently the conditioned air transport tubes are subject to being tightly kinked in hair-pin fashion during actual use. In essence the tube is virtually bent back upon itself as shown in FIG. 6 yet air flow through the tube must be maintained. A corrugated tube has been found to avoid kinking and shutting off the air flow but, nevertheless a thick outer casing will bunch on the inside of a hairpin bend at inner bend areas 16 and prevent such a bend from being formed or in the alternative cause even a corrugated tube to kink and shut off air flow. A thin casing 2–4 mils in thickness avoids the problem of bunching of material on the inside of a hair pin bend and therefore should preferably be selected for the casing material.

Also in the preferred embodiment both the materials of the casing as well as the corrugated tube should be a clear transparent polymeric resinous material. Examples of such material are polyproplene, polyetheylene, and copolymers, block polymers and blends of the same. Also suitably are polystyrene, polyvinyl acetate, polyvinyl choloride and other materials either alone or in blends with each other.

Such materials are well known in the art and are commonly referred to as plastics. Any such plastic or blend thereof can be utilized if it can be made to be flexible, clear and non-reactive to the gases to which it would normally be subjected. Such plastics or blends thereof should also be inert to cleaning solutions and other chemicals and reagents commonly used in hospitals. This is especially true since one very useful function of the present invention is to provide a smooth easily cleanable outer surface for the conditioned air transport tube.

Another reason for having the outer casing diameter greater than the diameter of the corrugated tube is to optimize the dead air space created there between. Generally it has been found that selecting an outer casing which has a volume of about 11.3 cubic inches per inch encasing a corrugated tube having about 4.9 cubic inches per inch is preferable. In essence then the linear volume of the insulating dead air space between the casing and the corrugated tube can be up to ten times or more the linear volume of the corrugated tube itself. This has been found to be desirable in sizing the insulating dead air space.

Moreover, it is essential that when a breathing tube is subjected to a hairpin bend the outer casing should not interfere with the ability of the breathing tube to be so shaped. Consequently a larger diameter casing permits such bending, keeping in mind that the casing is affixed at both of its ends to the respective ends of the corrugated tube to form the dead air space.

In addition it has been found that when the casing and the corrugated tube are positioned with the casing ensleeving the corrugated tube and the respective ends of each of the corrugated tube and the casing are affixed or sealed to define the annular air space therebetween that the casing should be slightly longer than the corrugated tube and longitudinally compressed slightly so that when sealed to the corrugated tubes the ends are juxtaposed. In essence then the casing the takes on a crinkled appearance. It has the appearance of a piece of paper that has been crumpled and then partially flattened. The benefit of having a casing which is not taut, but somewhat longer than the corrugated tube to which it is affixed is that when the conditioned air transport tube is subjected to a hairpin bend the casing does not interfere with such bending especially on the outside portion of the hairpin bend as shown at 17 on FIG. 6 where the casing normally would become taut and prevent further bending of the corrugated tube without rupturing or breaking loose from the corrugated tubing at one of its ends.

Proper sizing of the length of the outer casing is determined by selecting a casing length such that when it is sealed at its ends to a corrugated tube which it ensleeves the conditioned air transport tube formed thereby can be doubled back upon itself forming a hairpin bend therein and the outer casing is just taut across the outside surfaces of the corrugated tube which it encases. As previously noted FIG. 6 is illustrative of a hairpin bend in a conditioned air transport tube and illustrates the casing contacting the corrugation crests 5 of the corrugated tube 2 on the outer side of the hair pin bend.

Another important feature of the present invention relates to the relative surface area of the corrugated tube relative to the surface area of the envelope when the tube is in its relaxed or unstretched state. The total surface area of the casing surrounding the tube is substantially less than the enclosed surface area of the conditioned air transport tube because of the additional surface area provided by the corrugations. In some instances the surface area of the corrugated tubing may be as much as four times the surface of the envelope which encloses the corrugated breathing tube. Since the benefits derived from the use of the envelope are related to the radiation loss and the convection loss of heat from the tube the relative surface areas are of importance.

Those skilled in the art will also recognize that there are many tube arrangements used in medical applications for carrying conditional gases. For example, concentric tubes either corrugated or noncorrugated may be used. Also parallel corrugated or noncorrugated tubes may constitute the air transport tube for carrying conditional gases.

It will be understood that the foregoing are but a few examples of arrangements within the scope of the present invention and that various other arrangements also within the scope of the present invention will occur to those skilled in the art upon reading the disclosure set forth hereinbefore.

Having thus described the invention what is claimed is:

1. In a patient temperature control system, a conditioned air transport tube comprising an air impervious corrugated tube for carrying conditioned gases and an outer casing of first internal diameter for insulating the corrugated tube, said corrugated tube being located within said casing and having an outer diameter less than said internal diameter of said casing, said casing being of an overall length greater than the length of said corrugated tube and being sealed at its ends to the ends of the corrugated tube such that the casing is in a slightly longitudinally compressed state relative to said corrugated tube thereby defining an insulating dead air space between said corrugated tube and said casing, wherein the ratio of linear volumes of said casing and said corrugated tube are in the range of up to 10.0 to 1.0, said casing further being of smooth sidewall construction and being of thickness which is equal to or less than the thickness of said corrugated tube.

2. The conditioned air transport tube arrangement of claim 1 where the ratio of linear volumes of said casing and said corrugated tube are in the range of 2.2 to 1. The conditioned air transport tube arrangement of claim 1 where the ratio of linear volumes of said casing and said corrugated tube are in the range of 10.0 to 1.0.

3. An insulated conditioned air transport tube arrangement having an air impervious corrugated tube for carrying conditioned gases and an outer casing of first internal diameter for insulating the corrugated tube said corrugated tube being located within said casing and having an outer diameter less than said internal diameter of said casing, said casing being of an overall length greater than the length of said corrugated tube and being sealed at its ends to the ends of the corrugated tube such that the casing is in a slightly longitudinally compressed state relative to said corrugated tube thereby defining providing means for accommodating hairpin curves in said transport tube arrangement and defining an insulating dead air space between said corrugated tube and said casing, the volume of dead air space between said corrugated tube and said casing per unit length being in ratio to the volume of the corrugated tube per unit of length in the range of 0.5 to 1.0 to approximately 10.0 to 1.0, said casing further being of smooth sidewall construction to provide an easily cleanable surface and being of a thickness which is equal to or less than the thickness of said corrugated tube arrangement.

* * * * *